United States Patent [19]

Byrne et al.

[11] Patent Number: 5,395,033
[45] Date of Patent: Mar. 7, 1995

[54] ENDOSCOPIC SURGICAL INSTRUMENT WITH ELECTROMAGNETIC SENSOR

[75] Inventors: Mark T. Byrne, Loveland; Anthony A. Boiarski, Columbus; James E. Dvorsky, Hillaird; Julie B. Swick, Orient, all of Ohio

[73] Assignee: Ethicon, Inc., Somerville, N.J.

[21] Appl. No.: 248,587

[22] Filed: May 24, 1994

Related U.S. Application Data

[63] Continuation of Ser. No. 65,413, May 24, 1993, abandoned.

[51] Int. Cl.$^6$ .......................................... A61B 17/072
[52] U.S. Cl. ........................................ 227/175; 227/19
[58] Field of Search ............... 227/175, 19, 176, 177, 227/178, 180

[56] References Cited

U.S. PATENT DOCUMENTS

| | | | |
|---|---|---|---|
| 5,040,715 | 8/1991 | Green et al. | 227/180 X |
| 5,111,987 | 5/1992 | Moeinzadeh et al. | 227/176 X |
| 5,161,724 | 11/1992 | Radtke et al. | 227/1 |

OTHER PUBLICATIONS

Volkswagen, Scirocco, Cabriolet, Service Manuel, Robert Bentley, Cambridge, Mass., 1988, section 7, pp. 18-19.

Primary Examiner—Rinaldi I. Rada

[57] ABSTRACT

An endoscopic surgical instrument including a pair of jaws. An electromagnetic sensor disposed in said jaws to determine the relative position of said jaws.

14 Claims, 4 Drawing Sheets

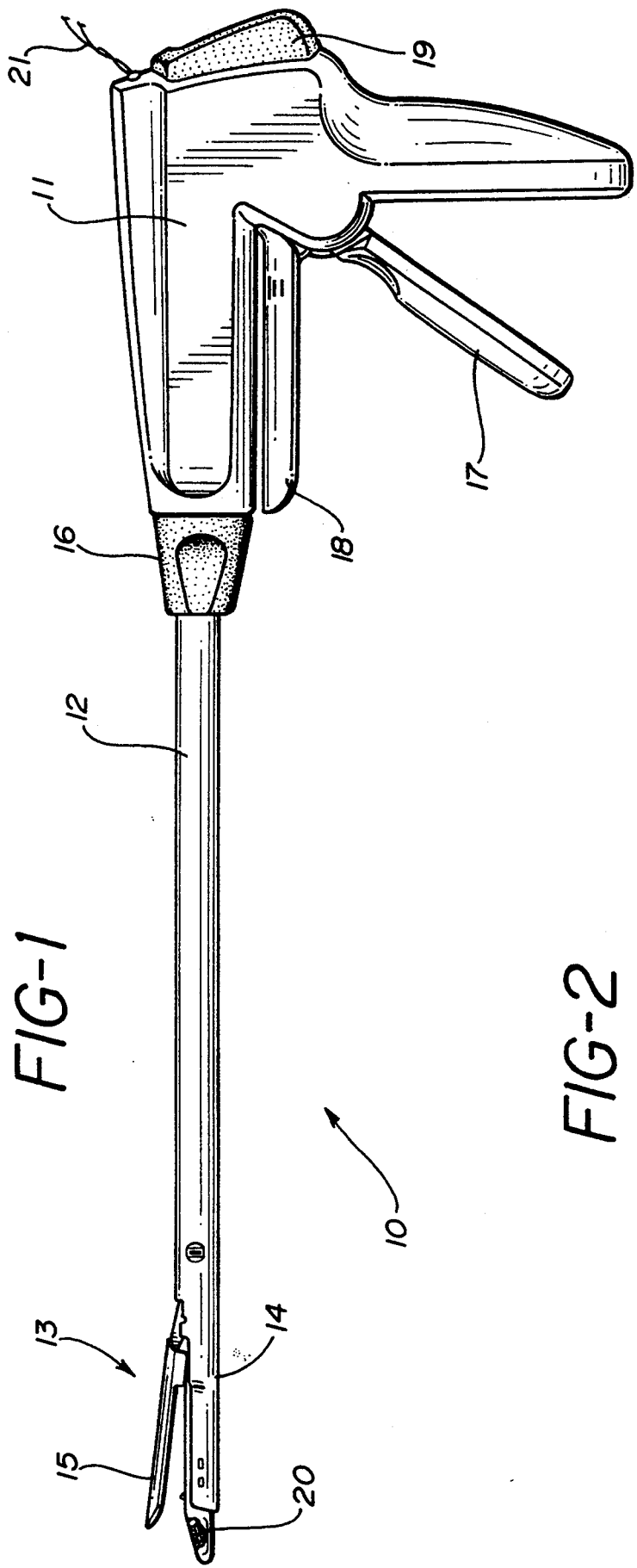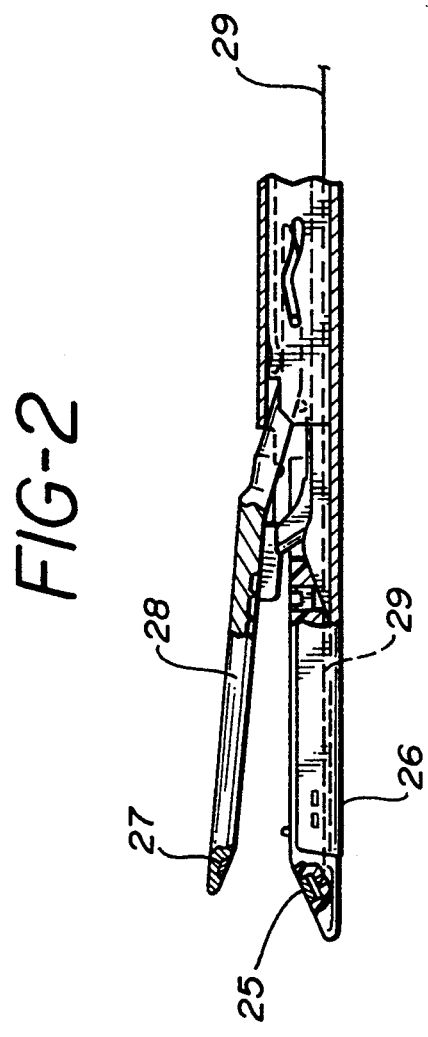

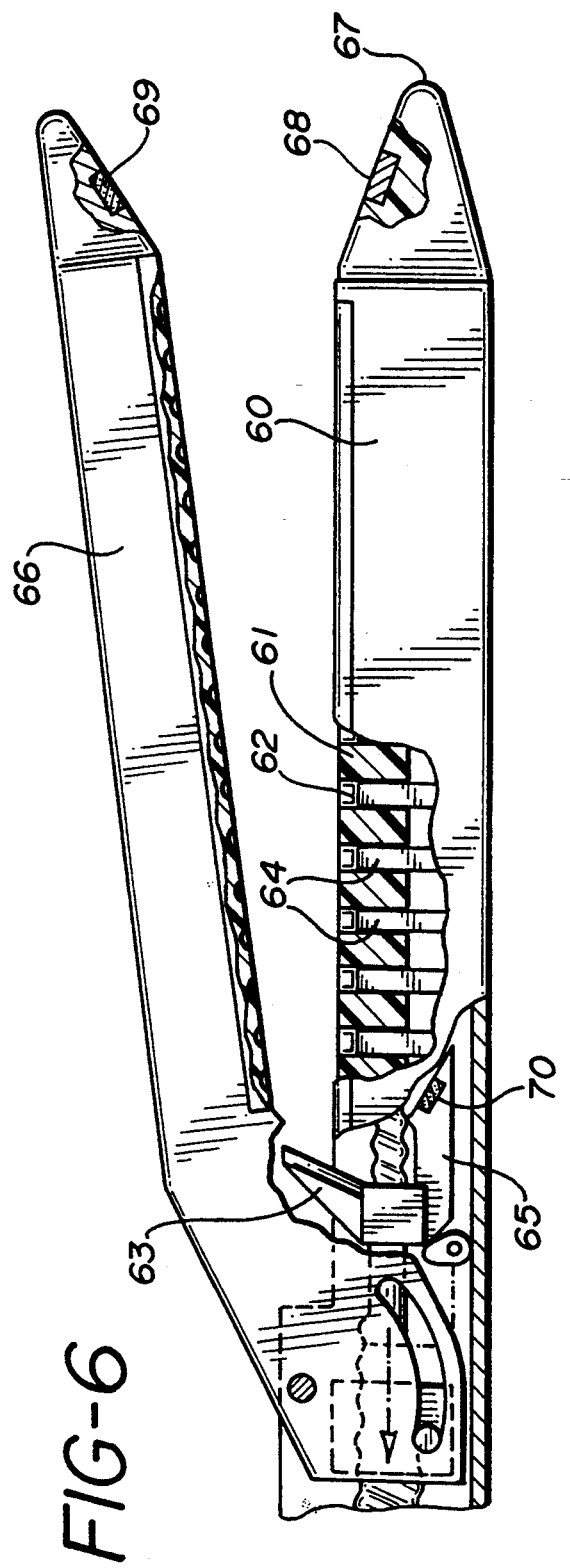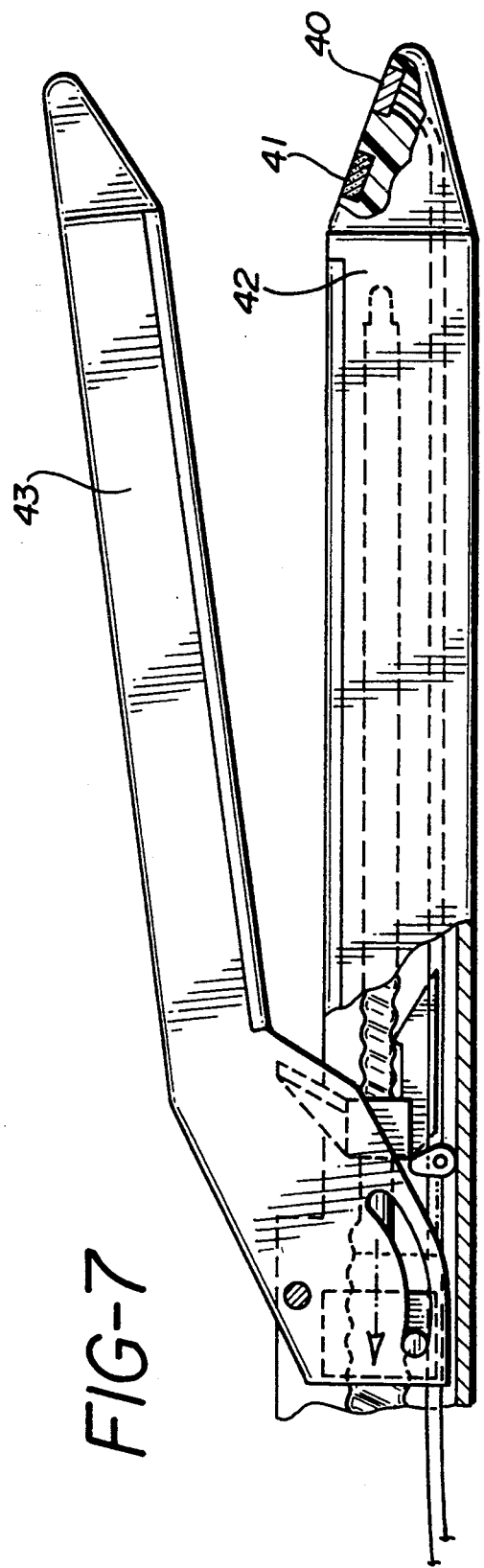

ENDOSCOPIC SURGICAL INSTRUMENT WITH ELECTROMAGNETIC SENSOR

This is a continuation of application Ser. No. 08/065,413, filed May 24, 1993, now abandoned.

FIELD OF THE INVENTION

This invention relates to an instrument for use in endoscopic procedures. More specifically, this invention relates to an instrument which includes an electromagnetic sensor in the head of the instrument to determine and/or measure tissue parameters during an endoscopic procedure.

BACKGROUND OF THE INVENTION

Endoscopic surgery has been gaining wide acceptance as an improved and cost effective technique for conducting certain surgical procedures. In endoscopic surgery, a trocar, which is a pointed piercing device, is inserted in the body with a cannula placed around the trocar. After the trocar accomplishes piercing of the abdominal walls, it is removed and the cannula remains in the body. Often multiple openings are produced in the body with a trocar. Through these cannula, endoscopic procedures are possible. An endoscopic instrument may be placed in one cannula, an appropriate viewing mechanism placed in another cannula and the fiber optics for illuminating the surgical field in yet another cannula. Generally, these endoscopic procedures take place under insufflation. As more is learned about endoscopic procedures and more instruments developed, the type of procedures that may be performed endoscopically will increase. Presently, typical procedures are gall bladder removal, tissue repair, and various sterilization procedures.

Many of the instruments used in endoscopic procedures are used to join tissue, grasp tissue, or otherwise manipulate tissue. Such instruments usually have a pair of jaws which are placed about the tissue to be manipulated, then the instrument is activated to manipulate the tissue. As can be appreciated, it is often quite difficult to be certain you have the jaws positioned correctly to manipulate the tissue and/or you have the right amount of tissue between the jaws in an appropriate position to manipulate the tissue.

It is an object of the present invention to provide an instrument that will allow the user to know when he has the jaws of an instrument appropriately placed about tissue. In certain embodiments, it is an object of the present invention to control an instrument so that it cannot be activated until the jaws are in an appropriate position about the tissue to be manipulated. In other embodiments, it is an object of the present invention to provide a feedback device for tissue fastening parameters.

SUMMARY OF THE INVENTION

The present invention provides a surgical instrument which has a pair of spaced apart and movable jaws. The instrument includes means for moving at least one jaw with respect to the other to accomplish a step in a surgical procedure. An electromagnetic sensor is disposed in one of the jaws and a permanent magnet target is disposed in the other of the jaws. The magnet produces a magnetic field between the jaws whereby the distance between the jaws may be determined.

The present invention is especially adaptable for use in a surgical stapler used to join body tissue. The stapler has a distal end and a proximal end. An elongated shaft portion connects the distal and proximal ends. The distal end has a pair of jaws with one of the jaws stationary and the other jaw movable with respect to the stationary jaw. The stationary jaw carries a plurality of staples. The movable jaw includes anvil means used for forming the staples. There are means disposed in the elongated shaft portion which extend from the proximal end to the distal end of the stapler to move the movable jaw into staple forming relationship with the stationary jaw. The instrument also includes actuating means to urge the staples towards the anvil means and form the staples to join tissue placed between the jaws. A permanent magnet is disposed adjacent the distal end of the movable jaw and facing the stationary jaw. A magnetoresistive sensor is disposed adjacent the distal end of the stationary jaw and facing the movable jaw. The magnet produces a magnetic field between the jaws and the sensor measures the variations in the magnetic field so that the distance between the jaws may be determined.

While the present invention will be further described in detail with regard to a surgical stapling instrument, it should be appreciated that the sensing and measuring device may be incorporated in other surgical instruments other than staplers. The present invention may be incorporated in any instrument that has a pair of jaws which are movable with respect to each other.

BRIEF DESCRIPTION OF THE DRAWINGS

FIG. 1 is a side elevational view of an endoscopic linear stapling and cutting instrument incorporating the sensing mechanism of the present invention;

FIG. 2 is an enlarged cross-sectional view of the stapling and cutting head of the instrument depicted in FIG. 1;

FIG. 6 is a side view of an embodiment of the distal end of a device incorporating the present invention;

FIG. 7 is a side view of an alternate embodiment of the distal end of an endoscopic instrument incorporating the sensor of the present invention.

DETAILED DESCRIPTION OF THE INVENTION

Figure 3A:
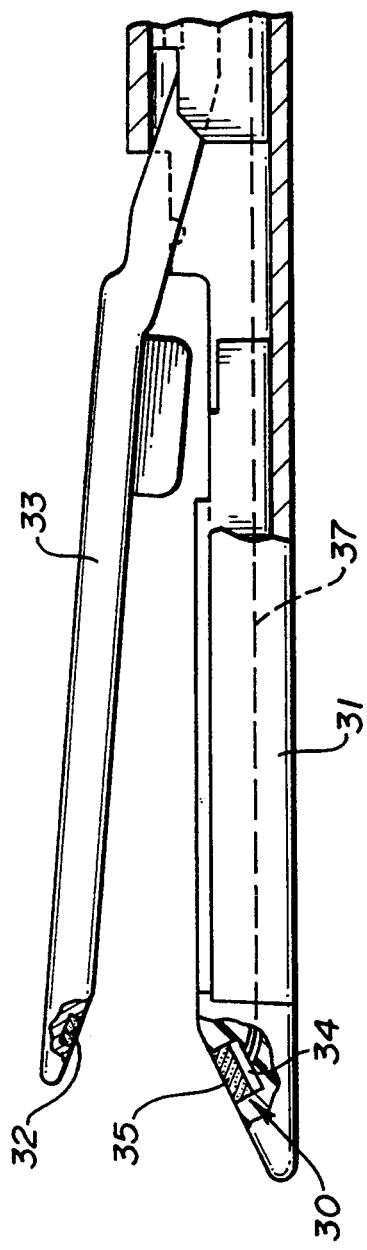
FIGS. 3a, b and c are side operational views of the staple holding portion and the anvil of the instrument depicted in FIG. 1.
Figure 3B:
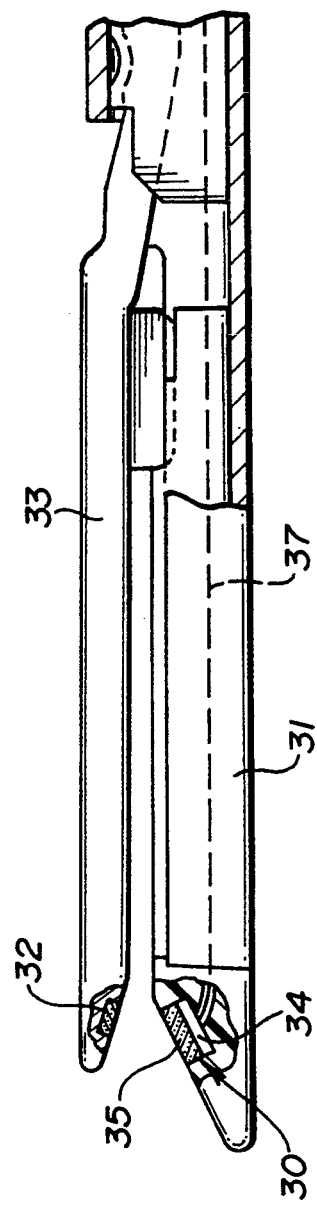
Figure 3C:
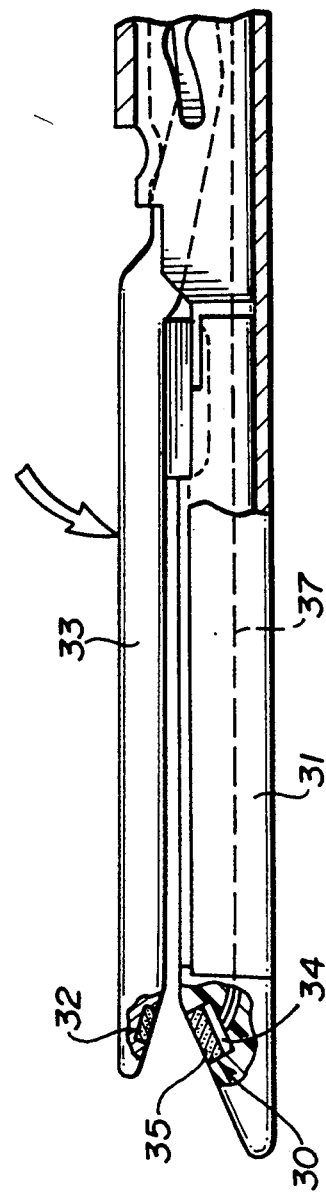

The invention will be described in detail with regard to an endoscopic surgical linear stapling and cutting instrument.

Referring to the drawings, in FIG. 1 there is shown an endoscopic linear stapler and cutting instrument 10 incorporating a sensing mechanism according to the present invention. The instrument comprises a handle portion 11 having an elongated shaft 12 extending from said handle portion. At the opposite end of the shaft is the stapling assembly 13. The stapling assembly comprises a stationary staple holding member 14 and a movable anvil member 15. The staple holding member carries four parallel rows of staples with the staples offset in adjacent rows. The staple holding member also includes a groove disposed between the center two rows of staples. The groove will accept a knife which is movable from the proximal end to the distal end of the staple holding member. The knife is used to sever tissue after it has been stapled as is well known in the art. Also, in this embodiment there is rotating means 16 disposed at the end of the handle portion from which the shaft extends. This rotating means allows the shaft as well as the business end, that is, the stapling assembly, to be rotated. In the handle portion, there is a first trigger 17 which is a closure trigger. This trigger is used to bring the anvil member into an appropriate position with respect to the staple holding member. The handle also includes a second or firing trigger 18. The firing trigger causes an appropriate mechanism located in the shaft to drive the staples out of the staple holder member and form the staples against the anvil member. The knife disposed in the distal end of the instrument is activated by this second trigger so that the knife moves between the staple lines and cuts tissue after the tissue has been joined. Disposed at the back of the handle of the instrument is an unlocking lever 19 which, when activated, opens the anvil member from the staple holding member. Such stapling instruments are more fully described in commonly assigned co-pending patent application Ser. Nos. 917,636 and 822,478, both of which are incorporated herein by reference.

Disposed in the business end of the instrument; that is, in the anvil member and the staple holding member, is the sensing mechanism 20 of the present invention. A suitable electrical power supply 21 is fed to the sensing mechanism. The sensing mechanism will be more fully described in conjunction with FIG. 2. As seen in FIG. 2, an electromagnetic sensor 25 is disposed in the distal end of the staple holding member 26. A permanent magnet 27 is disposed at the distal end of the anvil member 28. In this embodiment, a magneto-resistive sensor is used in the staple holding mechanism. Suitable electrical signals are fed to the sensor from an appropriate electrical source by the electric wires 29.

As can be appreciated, the sensor should be small; that is, have a diameter of about 3 to 5 millimeters with a thickness of 1 to 2 millimeters. The sensor should have a measurement range of from 0 to 5 milimeters with as much accuracy as possible. The sensor should be able to withstand irradiation so that the instrument may be sterilized by cobalt radiation or other techniques. It should also be resistant to interference caused by auxiliary magnetic fields, such as those generated by auxiliary equipment used in an operating room, as well as the magnetic field of the earth itself. Such suitable magneto-resistive sensors are available from the Philips Corporation and are identified as Magnetic Field Sensor KMZ10A and KMZ10B. Disposed in the anvil portion is a permanent magnet. Again, the magnet should be small enough to fit into the distal end of the anvil member and for the geometry of this embodiment it should have a magnetic field strength of about 400 gauss. Lower magnetic field strengths do not produce the desired measurement sensitivity over a 1 to 5 mm range and higher strength magnets tend to saturate the sensor at close range. As can be appreciated, as the anvil member is brought in closer proximity to the staple holding member, the magneto-resistive sensor detects the strength of the magnetic field produced by the permanent magnet. This signal can then be conveyed back to the operator. The signal will be converted into appropriate positioning information and may be displayed either on the handle of the instrument or on some other imaging display as desired. In certain embodiments, the information may be fed back to a controller to adjust staple height within the jaws or other parameters.

Figure 4:
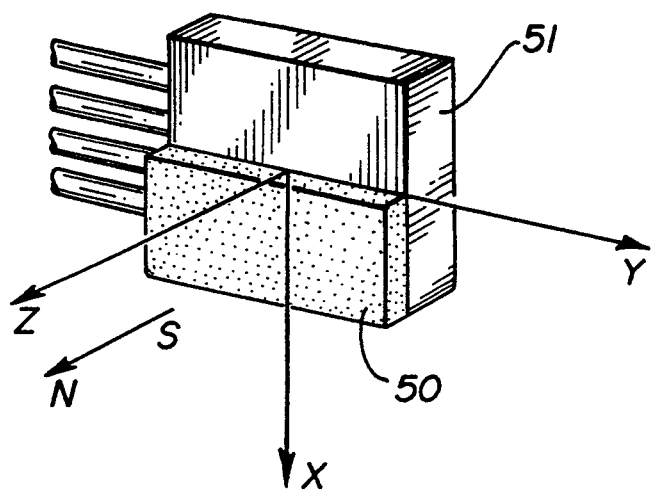
FIG. 4 is an enlarged perspective view of a sensor used in the devices of the present invention.

A preferred embodiment of the sensing device of the present invention is depicted in FIGS. 3a, b, and c. In this embodiment, there is a magnetically biased sensor 30 disposed in the staple holding member 31 of the instrument and a permanent magnet target 32 disposed in the anvil member 33 of the instrument. The sensor comprises a magneto-resistive sensor 34 and a biased magnet 35. The bias magnet is disposed on top of the sensor and faces the permanent target magnet disposed at the distal end of the anvil member. The bias magnet is used to provide a stabilizing magnetic field parallel to the sensors internal aligning field; i.e., the sensor's X axis. The stabilizing field is applied to strengthen the internal aligning field as a precaution against sensor flipping. Sensor flipping may occur if the sensor comes under a powerful magnetic field opposing the sensor's internal aligning field. The effect would be a reversal in polarity of the sensor output. As more clearly seen in FIG. 4, bias magnet 50 is attached to the top surface of the sensor and covers about half the surface of the sensor. The bias magnet is a plastic molded magnet approximately 2 millimeters by 4 millimeters × 0.76 millimeters in thickness. The bias magnet has its length parallel to the length of the sensor 51. The magnetic field of the bias magnet is oriented with its poles normal to the largest surface of the sensor and with the north pole facing upwardly. The field strength of the bias magnet is about 175 gauss. The bias magnet and sensor is embedded in the distal end of the staple holding member of the instrument and is disposed at an angle of about 12 degrees from the horizontal edge. The target magnet 52 is a plastic molded magnet. The size is approximately 4 millimeters by 5 millimeters by 1 millimeter thick and it is embedded in the distal portion of the anvil member. It is disposed at an angle of approximately 14 degrees from the horizontal. The magnetic field of the target magnet is oriented normal to the anvil surface with the south pole facing outwardly or downwardly. The field strength of this permanent magnet is about 400 gauss. The target magnet should be stronger than the bias magnet to improve overall sensitivity. In operation, the permanent magnet produces a magnetic field which is disposed outwardly towards the magneto-resistive sensor. As the anvil member is brought into closer proximity to the staple holding member, the magneto-resistive sensor will sense the strength and positioning of the magnetic field. The bias magnet also produces a magnetic field but a somewhat weaker magnetic field than the target magnet. This weaker magnetic field acts as a stabilizing field, improving the sensitivity in reading the gap between the sensor and the permanent magnet.

Figure 5:
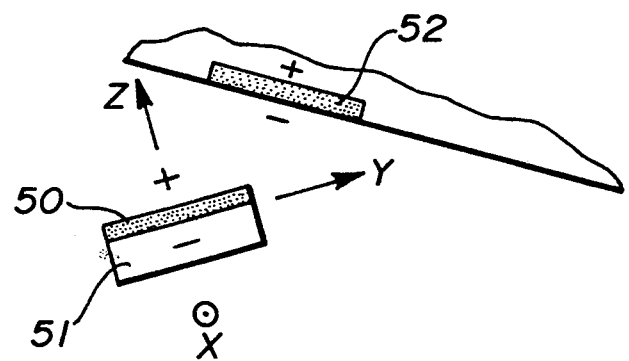
FIG. 5 is a side view depicting the spatial relationship between the sensor and the permanent magnet used in the present invention.

The location, strength and pole configuration of the magnets is important to obtain accurate readings. The magnetic field of the bias magnet is oriented with its poles normal to the surface of the sensor and with the north pole facing up as seen in FIG. 5. The magnetic field of the target magnet is oriented normal to the stationary jaw surface with the south pole facing down, as seen in FIG. 5. As previously mentioned, the magnetic field of the target magnet needs to be stronger than the magnetic field produced by the bias magnet to give desired sensitivity. By selecting the sensor and target magnet, one can control the X and/or Y components of the magnetic field produced by the target magnet which the sensor will detect and which will control the output of the sensor. It is desirable that a stabilizing field be established in the sensor's X axis and this is accomplished by the bias magnet. The magnetic field of the target magnet should have a strength of approximately 400 gauss and be greater than the magnetic strength of the bias magnet. As can be appreciated, the relative positions of the permanent magnet, the bias magnet and the sensing means must be controlled for the desired accuracy. As previously described with regard to FIG. 3a, the sensor is connected by electrical wires 37 to a suitable electrical power source. The reading from the sensor may be processed and converted to appropriate information and displayed on the handle of the instrument to allow the user to know the relative distance between the anvil member and the staple holding member. If desired, the sensor may be used to control the instrument in that the sensor signal may interlock with the trigger mechanisms to only allow firing of the mechanism when the anvil and staple holding members are in an appropriate position with respect to one another.

As seen in FIG. 6, in many stapling instruments, the staple holding member 60 includes a removable and disposable cartridge 61. The cartridge carries one or more rows of staples 62 and usually about 4 rows of staples with the staples in adjacent rows being offset. Often, there is a track between the two center rows to allow a knife 63 to pass down between rows of staples. Hence, on firing the staples, four rows are fired to join the tissue and then the tissue may be severed between the staples. The staple holding member holds the cartridge which holds appropriate driving mechanisms 64 for each staple. A wedge shaped member 65 moves through the cartridge to drive the staples from the cartridge through the tissue. The staples are formed against the anvil member 66 as is well known in the art. A magneto-resistive sensor may be held or embedded in the distal end of the cartridge; however, it is preferred that the staple holding member of the instrument be designed so that there is a permanent blunt end 67 on the staple holding member as shown in the drawings and with the cartridge being placed or fitted adjacent the blunt end. The sensor 68 is embedded in the blunt end so that it will always have the same relationship with respect to the permanent magnet 69. If the sensors are placed in the cartridge itself, it is conceivable that there could be slight variations from cartridge to cartridge which, of course, would reduce the accuracy of the sensor. An additional magnet 70 may be attached to the wedge shaped driving member 65. This additional magnet is used to signal an end to the cutting of the tissue between the formed staples. This allows the single sensor 68 to sense both tissue thickness and completion of the stapling and cutting operation. As can be appreciated, the sensor and magnets of the present invention are used to measure the spatial relationship between two surfaces and may be used for a variety of purposes; such as measuring tissue thickness, staple height, completion of an operation, the locking or unlocking of a mechanism and other operations used in endoscopic instruments.

Referring to FIG. 7 of the drawings, there is shown another embodiment of the sensor of the present invention. In this embodiment, both the magneto-resistive sensor 40 and the permanent magnet 41 are positioned on the staple holding member 42 the instrument. The anvil member 43 should be 400 series stainless steel or similar ferromagnetic material that will not effect and modify the configuration of the magnetic field being produced by the permanent magnet. As the anvil member is brought closer to the magnetic field of the permanent magnet, as when the jaws are closed the magnetic field produced by the permanent magnet, and observed by the sensor, has its strength modified. The magneto-resistive sensor will sense and measure this modification of magnetic field and produce a signal which can be converted to the desired information to control and measure the distance between the stationary staple holding member and the movable anvil member.

While the sensor described with regard to the Figures is a magneto-resistive sensor, that is, a sensor which is measuring changes in resistance induced by a changing magnetic field, other sensors may also be used such as a Hall Effect Sensor which produces a change in voltage due to the magnetic field and the like. The preferred embodiments of the present invention utilize a magneto-resistive sensor because of its higher sensitivity. Also the magneto-resistive sensors can withstand sterilization by various techniques; such as gamma radiation, autoclaving, and the like. The target magnet should not be so weak as not to be measurable nor so strong as to saturate the sensors. Permanent magnets having a strength of from about 300 to 500 gauss have been found satisfactory for gap ranges of from 1 to 5 mm. When using a bias magnet, it, of course, must be considerably weaker than a permanent magnet. A strength of about 175 gauss plus or minus 20 gauss has been found satisfactory for the bias magnet. If desired, the permanent magnet may be an electromagnet connected to a source operating at a known frequency. The resultant magnetic field will have the same frequency. The sensor will respond to changes in the magnetic field produced by the electromagnet. The use of such an electromagnet combined with a synchronous detector will eliminate interference from outside sources and other frequencies and produce a device having high sensitivity.

Although the invention has been described by way of examples and preferred embodiments, it will be evident that other adaptations and modifications may be employed without departing from the spirit and scope of the invention.

What is claimed is:

1. An endoscopic surgical instrument having a distal end, a proximal end for manipulating said distal end from outside the body cavity and an elongated shaft portion connecting said distal and proximal ends, said distal end including a pair of first and second spaced apart jaw members, said jaws members being movable with respect to each other, a plurality of staples disposed in one of said first or second jaw members, and an anvil disposed in said other jaw member, a magnetic target disposed in one of said first and second jaw members to produce an extended magnetic field and an electromagnetic sensor disposed in said other jaw member to measure variations in said magnetic field whereby the position of the jaw members with respect to each other may be determined.

2. An endoscopic surgical instrument according to claim 1 wherein the electromagnetic sensor is a magneto-resistive sensor.

3. An endoscopic surgical instrument according to claim 2 wherein the magneto-resistive sensor is magnetically biased.

4. An endoscopic surgical instrument according to claim 1 wherein variations in the magnetic field measure the distance between the jaw members.

5. An endoscopic surgical instrument according to claim 2 wherein the magneto-resistive sensor is gamma-radiation sterilizable.

6. An endoscopic surgical instrument according to claim 1 wherein the target magnet is a permanent magnet.

7. An endoscopic surgical instrument having a distal end for carrying out a step in a surgical procedure within a body cavity, a proximal end for manipulating said distal end from outside the body cavity and an elongated shaft portion connecting said distal and proximal ends, said distal end including a pair of spaced apart jaw members, one of said jaw members being stationary and the other of said jaw members being movable with respect to said stationary jaw member, a plurality of staples disposed in said stationary jaw member, a magnetic target disposed in said movable jaw to produce an extended magnetic field and a electromagnetic sensor disposed in said stationary jaw to measure variations in said magnetic field whereby the distance between the jaws may be determined.

8. An endoscopic surgical instrument according to claim 7 wherein the electromagnetic sensor is a magneto-resistive sensor.

9. An endoscopic surgical instrument according to claim 8 wherein the target magnet is a permanent magnet.

10. An endoscopic surgical instrument according to claim 8 wherein the magneto-resistive sensor is magnetically bias.

11. An endoscopic surgical stapler for joining body tissue, said stapler having a distal end, a proximal end, and an elongated shaft portion connecting said distal and proximal ends, said distal end comprising a pair of jaws, one of said jaws being stationary and the other of said jaws being movable with respect to said stationary jaw, a plurality of staples used to join tissue disposed in said stationary jaw, said movable jaw including anvil means for forming staples, means disposed in said elongated shaft portion and extending from the proximal end to the distal end of the stapler to move said movable jaw into forming relationship with said stationary jaw, actuating means disposed in said elongated shaft portion and extending from the proximal end to the distal end of the stapler to urge said staples towards said anvil means and form said staples to join tissue placed between said jaws, a magnetic target disposed adjacent the distal end of said movable jaw and facing said stationary jaw to produce a magnetic field between said jaws and an electromagnetic sensor disposed adjacent the distal end of said stationary jaw and facing said movable jaw to measure variations in said magnetic field whereby the distance between the jaws may be determined.

12. An endoscopic surgical staple according to claim 11 wherein the magnetic target is a permanent magnet.

13. An endoscopic surgical stapler according to claim 11 wherein the electromagnetic sensor is a magneto-resistive sensor.

14. An endoscopic surgical stapler according to claim 13 wherein the magneto-resistive sensor is magnetically biased.

* * * * *